United States Patent [19]
Marabout et al.

[11] Patent Number: 5,614,517
[45] Date of Patent: Mar. 25, 1997

[54] 8-OXO-5,8-DIHYDRO-6H-DIBENZO[A,G]-QUINOLIZINE-13-PROPANOIC ACID DERIVATIVES, THEIR PREPARATION AND THEIR THERAPEUTIC APPLICATION

[75] Inventors: Benoit Marabout, Chilly Mazarin; Mireille Sevrin, Paris; Jacques Froissant, Morée; Emmanuelle Dachary, Vitry sur Seine, all of France

[73] Assignee: Synthelabo, Le Plessis Robinson, France

[21] Appl. No.: 580,295

[22] Filed: Dec. 28, 1995

[30] Foreign Application Priority Data

Dec. 29, 1994 [FR] France .................... 94 15836

[51] Int. Cl.⁶ .................... A61K 31/535; A61K 31/495; A61K 31/44
[52] U.S. Cl. .................... 514/233.2; 514/255; 514/285; 546/71; 544/111; 544/125; 544/361
[58] Field of Search .................... 546/71; 544/111, 544/125, 361; 514/233.2, 255, 285

Primary Examiner—Amelia Owens
Attorney, Agent, or Firm—Foley & Lardner

[57] ABSTRACT

A compound of formula (I)

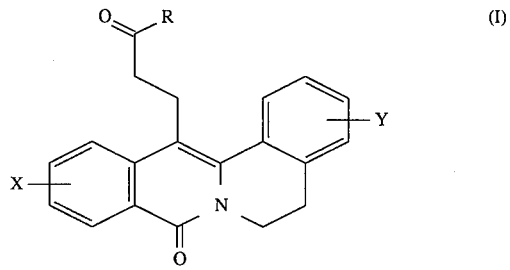

wherein
X is hydrogen, halogen, $C_1$–$C_3$ alkyl, trifluoromethyl, or $C_1$–$C_3$ alkoxy;
Y is hydrogen, halogen, $C_1$–$C_3$ alkyl, or $C_1$–$C_3$ alkoxy;
R is hydroxyl, methoxy, or amine; or a pharmaceutically acceptable acid addition salt thereof, useful for treating various neurological conditions.

7 Claims, No Drawings

8-OXO-5,8-DIHYDRO-6H-DIBENZO[A,G]QUINO-LIZINE-13-PROPANOIC ACID DERIVATIVES, THEIR PREPARATION AND THEIR THERAPEUTIC APPLICATION

The present invention relates to 8-oxo-5,8-dihydro-6H-dibenzo [a,g]quinolizine-13-propanoic acid derivatives, their preparation and their therapeutic application.

The present invention provides a compound of formula (I)

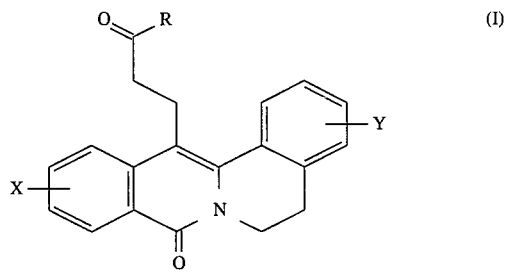

in which

X represents a hydrogen or halogen atom, a $C_1$–$C_3$ alkyl group, trifluoromethyl group, or a $C_1$–$C_3$ alkoxy in which case two such alkoxy groups X can be present, Y represents a hydrogen or halogen atom, a $C_1$–$C_3$ alkyl group or a $C_1$–$C_3$ alkoxy group, R represents: a hydroxyl group; a methoxy group; or a group of formula $NR_2R_3$ in which $R_2$ and $R_3$ each independently represents a hydrogen atom, a $C_1$–$C_4$ alkyl group, a 2-methoxyethyl group, a 2-aminoethyl group, a 3-aminopropyl group, a 2-(dimethylamino)ethyl group, a 3-(dimethylamino)propyl group or a 2-piperid-1-ylethyl group, or alternatively $R_2$ and $R_3$ form, together with the nitrogen atom to which they are attached, a morpholinyl or pyrrolidinyl ring or a piperazinyl ring optionally substituted in the 4-position with a methyl or (1,1-dimethyl-ethoxy)-carbonyl group in the form of the free base or of a pharmaceutically acceptable addition salt thereof.

In a preferred class of compounds X represents a hydrogen or chlorine atom, a methyl group, a trifluoromethyl group, or a $C_1$–$C_3$ alkoxy group in which case two such alkoxy groups X can be present, and Y represents a hydrogen or chlorine atom, a methyl group or a methoxy group.

The compounds may exist in the form of the free base or of addition salts with acids. Hydrochloride salts are preferred.

In accordance with the invention, the compounds of formula (I) are generally prepared by a process illustrated in general by Scheme 1 which follows.

An anhydride of formula (II), in which X is as defined above, is reacted with an imine of formula (III), in which Y is as defined above, generally in an aromatic solvent, for example toluene, at a temperature of 70° to 100° C. An acid of formula (IV) is obtained, which is esterified with thionyl chloride in methanol, generally at a temperature of 20° to 50° C., followed by conversion of the ester thus obtained, of formula (V), into an alcohol of formula (VI), for example via a mixed hydride such as sodium borohydride, in an ether solvent such as tetrahydrofuran. Next, the alcohol is oxidized to an aldehyde of formula (VII), for example according to the Swern method, the aldehyde is treated with methyl (dimethoxyphosphinyl)acetate (MDPA), generally in an ether solvent such as tetrahydrofuran, at a temperature of 20° to 75° C., the ester of formula (VIII) thus obtained is isolated and oxidized into an ester of formula (IX) generally using a quinone, for example 2,3-dichloro-5,6-dicyanocyclohexa-2,5-diene-1,4-diene, for example in an aromatic solvent such as toluene, at Scheme 1

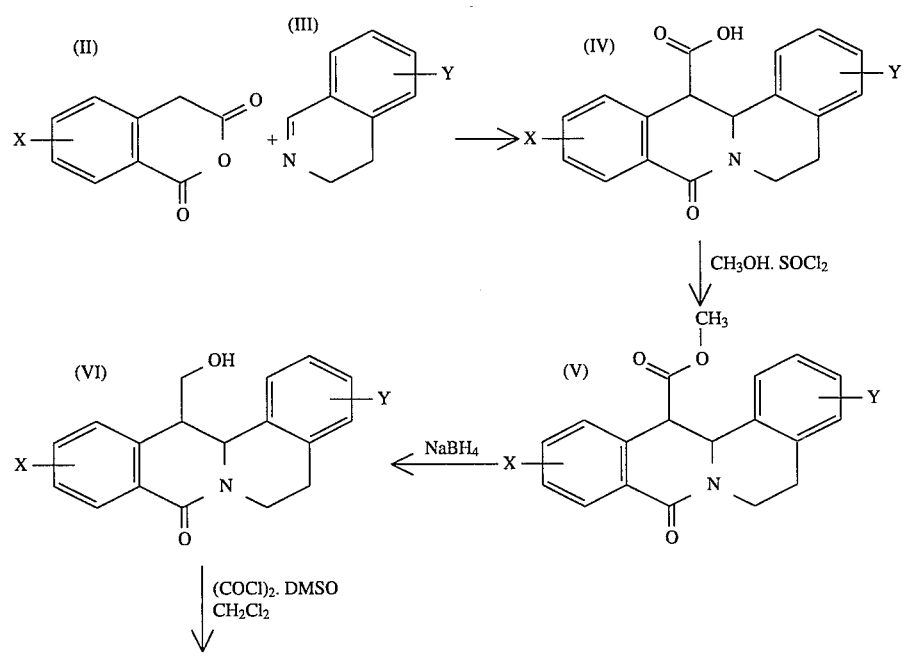

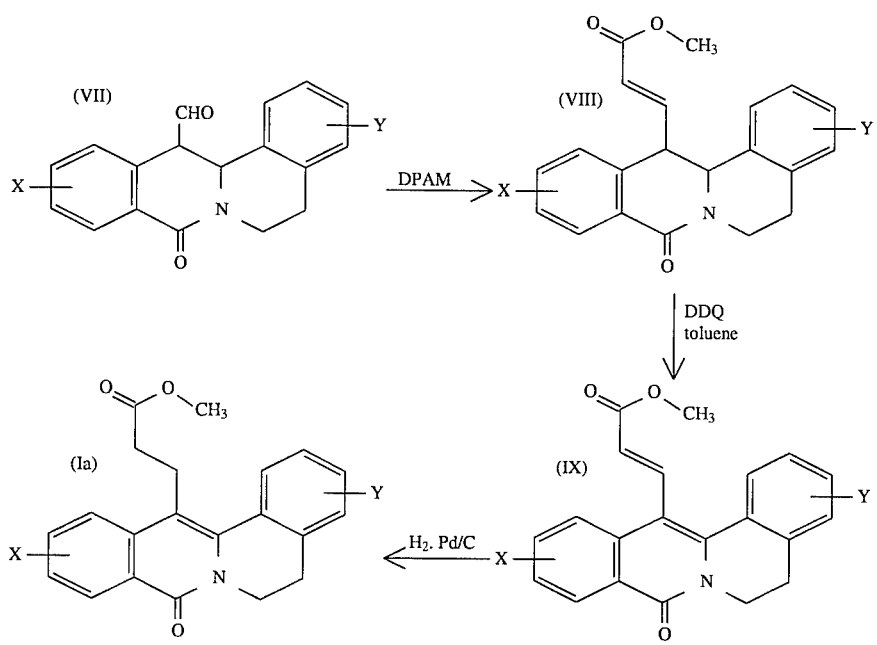

a temperature of 70° to 110° C., and, finally, the ester of formula (IX) is subjected to hydrogenation generally in the presence of palladium on charcoal, to obtain an ester of formula (Ia), which corresponds to a compound of formula (I) in which R represents a methoxy group.

This ester may then be converted as illustrated in general by Scheme 2: if a compound of formula (I) in which R represents a hydroxyl group is desired, the ester of formula (Ia) is hydrolysed generally in a basic medium to obtain an acid of formula (Ib) and, if a compound of formula (I) in which R represents a group of formula $NR_2R_3$ is desired, the acid of formula (Ib) is treated with an amine of formula $HNR_2R_3$, generally passing via the intermediate imidazolide prepared in situ using N,N'-carbonyldiimidazole.

For compounds of formula (I) in which X and Y are other than an alkoxy group, another process illustrated in general by Scheme 3 may be used.

A dibenzo[a,g]quinolizine of formula (X) is treated with phosphorus oxychloride, generally in N,N-dimethylformamide, at a temperature of 20° to 130° C., to obtain an aldehyde of formula (XI), which is treated with methyl (dimethoxyphosphinyl)acetate, generally in an ether solvent such as tetrahydrofuran, at a

Scheme 2

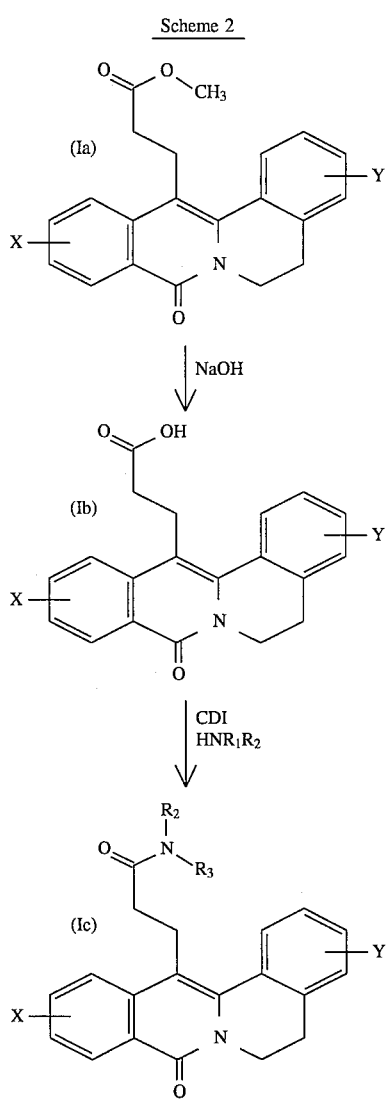

temperature of 20° to 65° C., to obtain an ester of formula (IX), the treatment of which compound is then completed as described with reference to Scheme 1.

The starting anhydride, of formula (II), is commercially available when X represents hydrogen, and in the other cases it may be prepared

Scheme 3

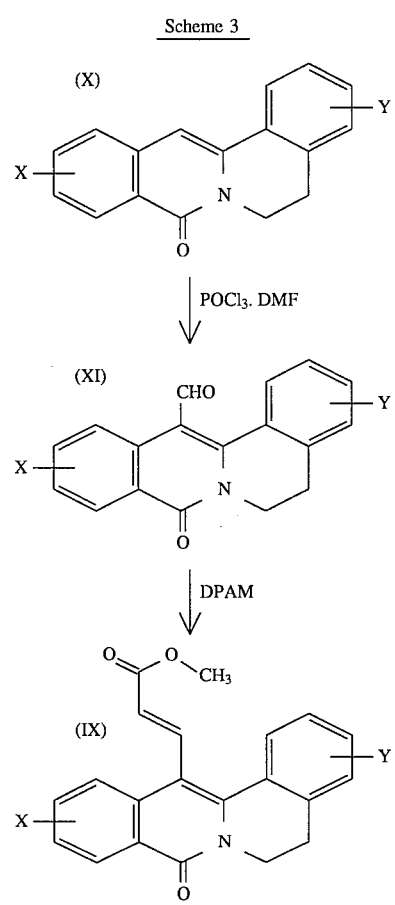

according to a method such as that described in *Arch. Pharm.* (1991) 324 509–518.

The substituted imines of formula (III) may be prepared by methods similar to those described in *Synthesis* (1974) 4 288–289 and *Heterocycles* (1982) 19 (4) 653–656.

The quinolizines of formula (X) may be prepared by methods similar to those described in *Synthesis* (1980) 10 845–847 and in *Tetrahedron Lett.* (1992) 33 (38) 5653–5654.

The Examples which follow illustrate the preparation of a few compounds of the invention. The elemental microanalyses and the IR and spectra confirm the structures of the compounds obtained. The numbers indicated in parentheses in the titles of the examples correspond to those in the 1st column of Table 1 given later.

EXAMPLE 1 (Compound No. 1)

Methyl 8-oxo-5,8-dihydro-6H-dibenzo[a,g]quinoliz-ine-13-propanoate 1.1 8-Oxo-5,8-dihydro-6H-dibenzo[a,g]quinolizine-13-carboxaldehyde 150 ml of dry N,N-dimethylformamide are cooled to 0° C., under an argon atmosphere, 5 ml (53.6 mmol) of phosphorus oxychloride are added dropwise, the mixture is stirred for 30 min at room temperature, 5 g (20.2 mmol) of 5,6-dihydro-8H-dibenzo[a,g]quinolizin-8-one are added, and the mixture is heated gradually to 110° C. and maintained at this temperature for 6 h.

The mixture is cooled to room temperature, the solvent is evaporated off under reduced pressure, ice and 30% sodium hydroxide are added to the residue, the mixture is extracted with dichloromethane, the organic phase is dried over sodium sulphate and filtered, and the solvent is evaporated off under reduced pressure. The residue is purified by chromatography on a column of silica gel, eluting with a cyclohexane/dichloromethane mixture ranging from 100/0 to 0/100, and then with a dichloromethane/ethyl acetate mixture ranging from 100/0 to 80/20.

After recrystallization from cyclohexane, 3.6 g (13.08 mmol) of aldehyde are isolated in the form of a white solid.
Melting point: 209–210° C.

1.2. Methyl (E)-3-(8-oxo-5,8-dihydro-6H-dibenzo[a,g] quinolizin-13-yl)prop-2-enoate 0.5 g (12.5 mmol) of a 60% suspension of sodium hydride is washed with pentane under an argon atmosphere, then a suspension thereof is prepared in 150 ml of dry tetrahydrofuran, the mixture is cooled with an ice bath, 2 g (11 mmol) of methyl (dimethoxyphosphinyl)acetate are added dropwise, the mixture is stirred for 15 min at 0° C., 2.78 g (10.1 mmol) of 8-oxo-5,8-dihydro-6H-dibenzo[a,g]quinolizine-13-carboxaldehyde are added, and the mixture is heated gradually to reflux and maintained at reflux for 6 h.

The mixture is cooled to room temperature, a few ml of methanol are added, the solvents are evaporated off under reduced pressure, ice, 200 ml of dichloromethane and 1M hydrochloric acid are added to the residue, the organic phase is separated out, dried over sodium sulphate and filtered, and the solvent is evaporated off under reduced pressure. The residue is purified by chromatography on a column of silica gel, eluting with a dichloromethane/ethyl acetate mixture ranging from 100/0 to 80/20 and the product is recrystallized from cyclohexane. 2.78 g (8.4 mmol ) of α,β-unsaturated ester are isolated in the form of white crystals.
Melting point: 201°–202.5°.

1.3 Methyl 8-oxo-5,8-dihydro-6H-dibenzo[a,g]quinolizine-13-propanoate

To a solution of 2.8 g (8.4 mmol) of methyl (E)-3-(8-oxo-5,8-dihydro-6H-dibenzo[a,g]quinolizin-13-yl)prop-2-enoate in 150 ml of acetic acid is added 0.23 g of 5% palladium on charcoal and the suspension is subjected to hydrogenation in a Parr apparatus at a pressure of about 0.32 MPa and at room temperature for 30 min, and then between 40 and 45° C. for 2 h 30.

The catalyst is separated out by filtration, the filtrate is concentrated under reduced pressure, 250 ml of dichloromethane, ice-cold water and saturated sodium hydrogen carbonate solution are added to the residue, the organic phase is separated out, washed with water, dried over sodium sulphate and filtered, and the solvent is evaporated off under reduced pressure. The residue is purified by chromatography on a column of silica gel, eluting with a dichloromethane/ethyl acetate mixture of from 100/0 to 70/30 and then with a dichloromethane/methanol mixture of from 95/5 to 90/10, and 2.8 g (8.4 mmol) of oily product are obtained. After recrystallization from cyclohexane, 2.5 g (7.5 mmol) of ester are obtained in the form of white crystals.
Melting point: 157–158.5° C.

EXAMPLE 2 (Compound No. 2)

8-Oxo-5,8-dihydro-6H-dibenzo[a,g]quinolizine-13-propanoic acid 2.45 g (7.35 mmol) of methyl 8-oxo-5,8-dihydro-6H-dibenzo[a,g]quinolizine-13-propanoate dissolved in 40 ml of ethanol are introduced into a 100 ml round-bottomed flask, 2 ml of aqueous 30% sodium hydroxide are added and the mixture is heated at reflux for 3 h.

The solvent is evaporated off under reduced pressure, the residue is taken up in water and 30% hydrochloric acid, and the solid which precipitates is collected by filtration, washed with water and dried.

2.2 g (6.89 mmol) of acid are obtained.
Melting point: 269–271 (decomposition).

EXAMPLE 3 (Compound No. 12)

N,N-Dimethyl -8-oxo-5,8-dihydro-6H-dibenzo[a,g] quinolizine-13-propanamide

A suspension of 1.2 g (3.76 mmol) of 8-oxo-5,8-dihydro-6H-dibenzo[a,g]quinolizine-13-propanoic acid in 100 ml of dichloromethane is prepared in a 250 ml round-bottomed flask placed under an argon atmosphere, 1.2 g (7.4 mmol) of N,N'-carbonyldiimidazole are added and the mixture is stirred at room temperature for 2 h.

The medium is saturated with gaseous dimethylamine for 1 min and the mixture is left stirring for 12 h. The solvent is evaporated off under reduced pressure, 200 ml of dichloromethane are added to the residue, the solution is washed with 1N hydrochloric acid, then with water, then with 1N sodium hydroxide and then again with water, dried over sodium sulphate and filtered, the solvent is evaporated off under reduced pressure and the residue is purified by chromatography on a column of silica gel, eluting with a dichloromethane/methanol mixture of from 100/0 to 90/10. After recrystallization from an acetonitrile/dichloromethane mixture, 0.93 g (2.68 mmol) of white solid is obtained.
Melting point: 192.5°–193.5° C .

EXAMPLE 4 (Compound No. 38)

10-Methoxy-8-oxo-5,8-dihydro-6H-dibenzo[a,g] quinolizine-13-propanoic acid 4.1. 10-Methoxy-8-oxo-5,8,13,13a-tetrahydro-6H dibenzo[a,g]quinolizine-13-carboxylic acid 8.1 g (42.15 mmol) of 7-methoxyhomophthalic anhydride dissolved in 350 ml of toluene are introduced into a 500 ml round-bottomed flask, 5.8 g (44.2 mmol) of 3,4-dihydroisoquinoline are added and the mixture is heated at reflux for 3 h. The mixture is allowed to cool to room temperature and is left to stand overnight.

The crystals formed are collected, washed with diethyl ether and dried under vacuum.

12.75 g (39.43 mmol) of acid as an approximately 90/10 trans/cis mixture are obtained.

Melting point: 227°–232° C.

4.2. Methyl trans-10-methoxy-8-oxo-5,8,13,13a-tetrahydro-6H-dibenzo[a,g]quinolizine-13-carboxylate A suspension of 14 g (43.3 mmol) of 10-methoxy-8-oxo-5,8,13,13a-tetrahydro-6H-dibenzo[a,g]quinolizine-13-carboxylic acid in 100 ml of methanol is prepared in a 500 ml three-necked round-bottomed flask, 3.2 ml (44.11 mmol) of thionyl chloride are added dropwise and the mixture is heated to reflux for 4 h.

The mixture is left to stand at room temperature overnight.

The crystals formed are collected, washed with diethyl ether and dried under vacuum.

11.5 g (34.08 mmol) of pure trans ester are obtained.

Melting point: 154.5°–157.5° C.

4.3. trans-13-(Hydroxymethyl)-10-methoxy-5,6,13,13a-tetrahydro-8H-dibenzo[a,g]quinolizin-8-one A suspension is prepared from 9.85 g (29.2 mmol) of methyl trans-10-methoxy-8-oxo-5,8,13,13a-tetrahydro-6H-dibenzo[a,g]quinolizine-13-carboxylate and 75 ml of tetrahydrofuran in a 250 ml round-bottomed flask, 4.68 g (146 mmol) of methanol and 5.52 g (146 mmol) of sodium borohydride are successively added, and the mixture is stirred at room temperature for 4 h.

The mixture is hydrolysed by adding 100 ml of water, it is extracted with three times 150 ml of dichloromethane, the organic phase is dried over sodium sulphate, the solvent is evaporated off under reduced pressure and the residue is purified by chromatography on a column of silica gel, eluting with a dichloromethane/ethyl acetate mixture of from 100/0 to 50/50.

After evaporation of the solvents, the crystals are taken up in diethyl ether and 8.3 g (26.83 mmol) of trans alcohol are finally obtained.

Melting point: 180°–181.5° C.

4.4. 10-Methoxy-8-oxo-5,8,13,13a-tetrahydro-6H-dibenzo[a,g]quinolizine-13-carboxaldehyde 20.2 g (159 mmol) of oxalyl chloride and 100 ml of dichloromethane are introduced into a 500 ml three-necked round-bottomed flask placed under an argon atmosphere, the mixture is cooled to −70° C., 16.36 g (209 mmol) Of dimethyl sulphoxide dissolved in 50 ml of dichloromethane are added dropwise, and the system is stirred at −70° C. for 15 min.

8.2 g (26.68 mmol) of trans-13-(hydroxymethyl)-10-methoxy-5,6,13,13a-tetrahydro-8H-dibenzo[a,g]quinolizin-8-one dissolved in 150 ml of dichloromethane are added over 30 min and the mixture is stirred at −60° C. for 30 min.

21.2 g (209 mmol) of triethylamine dissolved in 50 ml of dichloromethane are added and the mixture is allowed to warm to room temperature.

The mixture is poured onto 500 ml of saturated aqueous sodium chloride solution and extracted with three times 200 ml of dichloromethane. The organic phase is dried over sodium sulphate and filtered, and the solvents are evaporated off under reduced pressure. The residue is purified by chromatography on a column of silica gel, eluting with a 2/1 and then 1/0 dichloromethane/cyclohexane mixture, and then with a dichloromethane/ethyl acetate mixture of from 90/10 to 50/50.

After recrystallization from a mixture of ethyl acetate and petroleum ether, 8.02 g (26.09 mmol) of aldehyde are obtained as an 80/20 trans/cis mixture.

Melting point: 146°–149° C.

4.5. Methyl (E)-3-(10-methoxy-8-oxo-5,8,13,13a-tetrahydro-6H-dibenzo[a,g]quinolizin-13-yl)prop-2-enoate 1.3 g (32.5 mmol) of sodium hydride as a 60% suspension in oil is washed with pentane in a 500 ml three-necked round-bottomed flask, the washed sodium hydride is suspended in 200 ml of tetrahydrofuran, the suspension is cooled to 0° C., 5.2 g (28.55 mmol) of methyl (dimethoxyphosphinyl)acetate are added dropwise and the stirring is continued at about 10° C. for 20 min.

8 g (26 mmol) of 10-methoxy-8-oxo-5,8,13,13a-tetrahydro-6H-dibenzo[a,g]quinolizine-13-carboxaldehyde are added and the mixture is heated at reflux for 4 h 30.

The mixture is allowed to cool to room temperature, a few drops of methanol are added, the solvents are evaporated off under reduced pressure, 250 ml of water are added to the residue and the mixture is extracted with three times 150 ml of dichloromethane. The organic phase is dried over sodium sulphate and filtered, the solvent is evaporated off under reduced pressure and the residue is purified by chromatography on a column of silica gel, eluting with a 1/2 to 3/1 ethyl acetate/cyclohexane mixture, and 6.55 g (18.02 mmol) of ester are obtained in the form of an oil which is used without further purification in the following step.

4.6. Methyl (E)-3-(10-methoxy-8-oxo-5,8-dihydro-6H-dibenzo[a,g]quinolizin-13-yl)prop-2-enoate 5.5 g (15.13 mmol) of methyl (E)-3-(10-methoxy-8-oxo-5,8,13,13a-tetrahydro-6H-dibenzo[a,g]quinolizin-13-yl)prop-2-enoate are dissolved in 150 ml of toluene in a 500 ml round-bottomed flask, 5.15 g (22.7 mmol) of 2,3-dichloro-5,6-dicyanocyclohexa-2,5-diene-1,4-diene are added and the mixture is heated at reflux for 2 h 30.

The mixture is allowed to cool to room temperature, the solvent is evaporated off under reduced pressure and the residue is purified by chromatography on a column of silica gel, eluting with a dichloromethane/ethyl acetate mixture of from 100/0 to 80/20. The oil obtained is taken up in a mixture of diethyl ether and petroleum ether, and 3.31 g (9.2 mmol) of compound are isolated in the form of orange-yellow crystals.

Melting point: 149°–152° C.

4.7. Methyl 10-methoxy-8-oxo-5,8-dihydro-6H-dibenzo[a,g]quinolizine-13-propanoate To a solution of 3.5 g (9.68 mmol) of methyl (E)-3-(10-methoxy-8-oxo-5,8-dihydro-6H-dibenzo[a,g]quinolizin-13-yl)prop-2-enoate in 100 ml of acetic acid is added 0.5 g of 5% palladium on charcoal and the suspension is subjected to hydrogenation in a Parr apparatus at a pressure of about 0.32 MPa between 50° and 60° C. for 3 h.

The mixture is allowed to cool to room temperature, the catalyst is separated out by filtration, the filtrate is concentrated under reduced pressure, 250 ml of dichloromethane are added to the residue, the solution is washed with saturated aqueous sodium hydrogen carbonate solution, dried over sodium sulphate and filtered, and the solvents are evaporated off under reduced pressure. The residue is purified by chromatography on a column of silica gel, eluting with a dichloromethane/ethyl acetate mixture of from 100/0 to 50/50 and 3.4 g (9.36 mmol) of ester are obtained in the form of an oil which is used without further purification in the following step.

4.8. 10-Methoxy-8-oxo-5,8-dihydro-6H-dibenzo[a,g]quinolizine-13-propanoic acid 3.4 g (9.36 mmol) of methyl 10-methoxy-8-oxo-5,8-dihydro-6H-dibenzo[a,g]quinolizine-13-propanoate dissolved in 50 ml of ethanol are introduced into a 100 ml round-bottomed flask, 3 ml of aqueous 30% sodium hydroxide are added and the mixture is heated at reflux for 3 h.

The solvents are evaporated off under reduced pressure, water and 30% hydrochloric acid are added to the residue, and the solid which precipitates is collected, washed with water and dried.

3.0 g (8.58 mmol) of acid are finally obtained.
Melting point: 260°–264° C.

EXAMPLE 5 (Compound No. 40)

10-Methoxy-N-methyl-8-oxo-5,8-dihydro-6H-dibenzo[a,g]quinolizine-13-propanamide

A suspension of 1 g (2.86 mmol) of 10-methoxy-8-oxo-5,8-dihydro-6H-dibenzo[a,g]quinolizine13-propanoic acid in 100 ml of dichloromethane is prepared in a 250 ml round-bottomed flask under an argon atmosphere, 0.93 g (5.72 mmol) of N,N'-carbonyldiimidazole is added and the mixture is stirred at room temperature for 2 h.

The mixture is then saturated with gaseous methylamine for 1 min and stirring is continued for 22 h. The solvent is evaporated off under reduced pressure, 200 ml of dichloromethane are added to the residue, the solution is washed with water, then with 1N hydrochloric acid, then with 1N sodium hydroxide and then again with water, dried over sodium sulphate and filtered, the solvent is evaporated off under reduced pressure and the residue is purified by chromatography on a column of silica gel, eluting with a dichloromethane/methanol mixture of from 100/0 to 97/3.

After recrystallization from ethyl acetate, 0.43 g (1.19 mmol) of white solid is finally obtained.
Melting point: 182°–183° C.

The table which follows illustrates the chemical structures and the physical properties of a few compounds according to the invention.

TABLE (I)

| No. | X | Y | R | Salt | m.p. (°C.) |
|-----|---|---|---|------|------------|
| 1 | H | H | $OCH_3$ | — | 157–158.5 |
| 2 | H | H | OH | — | 269–271 (d) |
| 3 | H | H | $NH_2$ | — | 277–278 |
| 4 | H | H | $NHCH_3$ | — | 221–222.5 |
| 5 | H | H | $NHCH_2CH_3$ | — | 171–172.5 |
| 6 | H | H | $NH(CH_2)_2CH_3$ | — | 135–136 |
| 7 | H | H | $NH(CH_2)_3CH_3$ | — | 139–140 |
| 8 | H | H | $NH(CH_2)_2OCH_3$ | — | 140–141 |
| 9 | H | H | $NH(CH_2)_2NH_2$ | HCl | 149–152 |
| 10 | H | H | $NH(CH_2)_2N(CH_3)_2$ | HCl | 231–232 |
| 11 | H | H | $NH(CH_2)_3N(CH_3)_2$ | HCl | 220.6–220.7 |
| 12 | H | H | $N(CH_3)_2$ | — | 192.5–193.5 |
| 13 | H | H | $N(CH_2CH_3)_2$ | — | 139–140 |
| 14 | H | H | $N[(CH_2)_2CH_3]_2$ | — | 136–137 |
| 15 | H | H | $N[(CH_2)_3CH_3]_2$ | — | 101–102 |
| 16 | H | H | $N(CH_3)(CH_2)_3N(CH_3)_2$ | HCl | 202–203 |
| 17 | H | H | pyrrolidin-1-yl | — | 184–185 |
| 18 | H | H | morpholin-4-yl | — | 178.5–179.5 |
| 19 | H | H | piperazin-1-yl | HCl | 214–215 |
| 20 | H | H | 4-methylpiperazin-1-yl | HCl | 284–285 |
| 21 | H | H | 4-Boc-piperazin-1-yl | — | 95–100 |

TABLE-continued

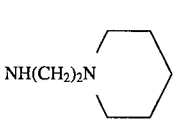

| No. | X | Y | R | Salt | m.p. (°C.) |
|---|---|---|---|---|---|
| 22 | H | H | NH(CH$_2$)$_2$N(cyclohexyl) | HCl | 167–168 |
| 23 | H | 1-CH$_3$ | NHCH$_3$ | — | 198–200 |
| 24 | H | 2-CH$_3$ | NHCH$_3$ | — | 180.5–182 |
| 25 | H | 2-CH$_3$ | N(CH$_3$)$_2$ | — | 156–157 |
| 26 | H | 2-OCH$_3$ | NHCH$_3$ | — | 192.5–194 |
| 27 | H | 2-OCH$_3$ | NH(CH$_2$)$_2$N(CH$_3$)$_2$ | HCl | 222–224 |
| 28 | H | 2-Cl | NHCH$_3$ | — | 182–184 |
| 29 | H | 2-Cl | N(CH$_3$)$_2$ | — | 192–194 |
| 30 | H | 2-Cl | N(CH$_2$CH$_3$)$_2$ | — | 214–216 |
| 31 | H | 2-Cl | NH(CH$_2$)$_2$N(CH$_3$)$_2$ | HCl | 207–209 |
| 32 | H | 3-CH$_3$ | N(CH$_3$)$_2$ | — | 185–186 |
| 33 | H | 3-OCH$_3$ | NHCH$_3$ | — | 165–166.5 |
| 34 | H | 4-CH$_3$ | NHCH$_3$ | — | 198–200 |
| 35 | H | 4-CH$_3$ | N(CH$_3$)$_2$ | — | 188–190 |
| 36 | 10-Cl | H | NHCH$_3$ | — | 209–210 |
| 37 | 10-Cl | H | N(CH$_3$)$_2$ | — | 221–224 |
| 38 | 10-OCH$_3$ | H | OH | — | 260–264 |
| 39 | 10-OCH$_3$ | H | N(CH$_3$)$_2$ | — | 213.5–215 |
| 40 | 10-OCH$_3$ | H | NHCH$_3$ | — | 182–183 |
| 41 | 10-OCH$_3$ | H | NH(CH$_2$)$_2$N(CH$_3$)$_2$ | HCl | 212–214 |
| 42 | 10-CH$_3$ | H | NHCH$_3$ | — | 172–174 |
| 43 | 10-CH$_3$ | H | N(CH$_3$)$_2$ | — | 229–231 |
| 44 | 10-CF$_3$ | H | NHCH$_3$ | — | 224–225 |
| 45 | 10-CF$_3$ | H | N(CH$_3$)$_2$ | — | 237–238 |
| 46 | 11-OCH$_3$ | H | NHCH$_3$ | — | 156.5–157 |
| 47 | 10-Cl | 2-CH$_3$ | NHCH$_3$ | — | 199–201 |
| 48 | 10-OCH$_3$ | 2-OCH$_3$ | NHCH$_3$ | — | 209–211 |
| 49 | 10-OCH$_3$ | 2-OCH$_3$ | N(CH$_3$)$_2$ | — | 196–198 |
| 50 | 10-Cl | 2-OCH$_3$ | NHCH$_3$ | — | 225–227 |
| 51 | 10-OCH$_3$ | 2-CH$_3$ | NHCH$_3$ | — | 205–207 |
| 52 | 10-OCH$_3$ | 2-CH$_3$ | N(CH$_3$)$_2$ | — | 188–190 |
| 53 | 10-CF$_3$ | 2-CH$_3$ | NHCH$_3$ | — | 238–240 |
| 54 | 10-CF$_3$ | 2-OCH$_3$ | NHCH$_3$ | — | 231–233 |
| 55 | 10-Cl | 2-Cl | NHCH$_3$ | — | 235–237 |
| 56 | 10-CF$_3$ | 2-Cl | NHCH$_3$ | — | 264–266 |
| 57 | 10,11-(OCH$_3$)$_2$ | H | NHCH$_3$ | — | 202–203 |

Note:
In the formula of the group R for compound No. 21, "Boc" denotes a (1,1-dimethylethoxy) carbonyl group.

In the "salt" column, "—" denotes a compound in base form and "HCl" denotes a hydrochloride.

In the final column, "(d)" denotes a melting point with decomposition.

The compounds of the invention were subjected to pharmacological tests which demonstrated their advantage as therapeutically active substances.

Study of the membrane binding with respect to a population of ω-(benzodiazepine) receptors associated with the GABA$_A$ receptors containing the α$_5$ sub-unit These receptors may be labelled selectively in rat hippocampus membranes incubated in the presence of [$^3$H] flumazenil and 5 μM zolpidem (in order to mask the other ω receptor subtypes).

The compounds formed the subject of an in vitro study with regard to their affinity for these receptors labelled with [$^3$H]flumazenil.

The animals used were OFA male rats (Iffa Credo) weighing 200 to 250 g. After decapitation, the hippocampus is removed and ground using an Ultra-Turrax™ or Polytron™ machine for 20 s at 6/10 of the maximum speed in 80 volumes of 50 mM tris buffer at a pH adjusted to 7.4 with hydrochloric acid, and containing 120 mM of sodium chloride and 5 mM of potassium chloride.

The binding with [$^3$H]flumazenil (1 nM; specific activity: 80–87 Ci/mmol; Du Pont de Nemours/New England Nuclear) is determined by incubation of 200 μl of membrane suspension in a final volume of 1 ml of buffer containing 5 μM of zolpidem and the test compound. After incubation for 45 min at 0° C., the membranes are recovered by filtration on Whatman GF/B™ filters, which are washed twice with 5 ml of ice-cold buffer. The amount of radioactivity retained by the filter is measured by liquid scintigraphy.

The specific binding of [$^3$H]flumazenil is defined as the amount of radioactivity retained on the filters and which may be inhibited by coincubation with 1 µM flunitrazepam. For each concentration of test compound the percentage of inhibition of the binding of [$^3$H]flumazenil is determined, followed by determination of the IC$_{50}$, the concentration which inhibits the specific binding by 50%.

The most active compounds of the invention in this test have an IC$_{50}$, value of the order of 1 to 100 nM.

Study of the membrane binding with respect to $\omega_2$ (type II benzodiazepine.) recptors associated with the GABA$_A$ receptors mainly containing the $\alpha_2$ and $\alpha_3$ sub-units The affinity of the compounds for the $\omega_2$ receptors of the spinal column was determined according to a variant of the method described by S. Z. Langer and S. Arbilla in *Fund. Clin. Pharmacol.* (1988) 2 159–170, using [$^3$H]flumazenil instead of [$^3$H]diazepam as the radioligand.

Spinal column tissue is homogenized for 60 s in 30 volumes of ice-cold buffer (50 mM Tris/HCl, pH 7.4, 120 mM NaCl, 5 mM KCl) followed, after dilution to ⅓, by incubation of the suspension with [$^3$H]flumazenil (specific activity: 78 Ci/mmol; New England Nuclear) at a concentration of I nM and with the compounds of the invention, at various concentrations, in a final volume of 525 µl . After incubation for 30 min at 0° C., the samples are filtered under vacuum on Whatman GF/B™ filters and are immediately washed with ice-cold buffer. The specific binding of the [$^3$H]flumazenil is determined in the presence of 1 µM unlabelled diazepam. The data are analysed according to the usual methods and the IC$_{50}$, the concentration which inhibits the binding of the [$^3$H]flumazenil by 50%, is calculated.

In this test, the IC$_{50}$ values of the compounds of the invention are between 1 and 500 nM.

Study of the Membrane Binding with Respect to $\omega_1$ (Type I Benzodiazepine) Receptors Associated with the GABA$_A$ Receptors Containing the $\alpha_1$ Sub-Unit The affinity of the compounds for the $\omega_1$, receptors from the cerebellum was determined according to a variant of the method described by S. Z. Langer and S. Arbilla in *Fund. Clin. Pharmacol.* (1988) 2 159–170, using [$^3$H]flumazenil instead of [$^3$H]diazepam as the radioligand.

Cerebellum tissue is homogenized for 60 s in 120 volumes of ice-cold buffer (50 mM Tris/HCl , pH 7.4, 120 mM NaCl, 5 mM KCl) followed after dilution to ⅓, by incubation of the suspension with [$^3$H]flumazenil (specific activity: 78 Ci/mmol; New England Nuclear) at a concentration of 1 nM and with the compounds of the invention, at various concentrations, in a final volume of 525 µl . After incubation for 30 min at 0° C., the samples are filtered under vacuum on Whatman GF/B™ filters and are immediately washed with ice-cold buffer. The specific binding of the [$^3$H] flumazenil is determined in the presence of 1 µM unlabelled diazepam. The data are analysed according to the usual methods and the IC$_{50}$, the concentration which inhibits the binding of the [$^3$H]flumazenil by 50%, is calculated In this test, the IC$_{50}$, values of the compounds of the invention are between 1 and 500 nM.

The results of the tests carried out on the compounds of the invention show that, in vitro some of them selectively displace [$^3$H]flumazenil from its membrane binding sites with respect to a population of ω (benzodiazepine) receptors associated with the GABA$_A$ receptors containing the $\alpha_5$ sub-unit, when compared with the receptor subtypes associated with the GABA$_A$ receptors containing the $\alpha_1$ sub-unit, and when compared with a population of $\omega_2$ (type II benzodiazepine) receptors associated with the GABA$_A$ receptors mainly containing the $\alpha_2$ and $\alpha_3$ sub-units.

Other compounds have a strong affinity for the $\alpha_5$, $\alpha_1$, $\alpha_2$ and $\alpha_3$ sub-units and are not selective. In other words the compounds have a strong affinity for the membrane binding sites of [$^3$H] flumazenil with respect to a population of ω (benzodiazepine) receptors associated with the GABA$_A$ receptors containing the $\alpha_5$ sub-unit, a strong, average or weak affinity for the $\omega_1$ (type I benzodiazepine) receptor subtypes associated with the GABA$_A$ receptors containing the $\alpha_1$, sub-unit, a strong, average or weak affinity for a population of $\omega_2$ (type II benzodiazepine) receptors associated with the GABA$_A$ receptors mainly containing the $\alpha_2$ and $\alpha_3$ sub-units.

The selectivity represented by the $\omega_1$-cerebellum IC$_{50}$/ω-hippocampus IC$_{50}$ ratio is between 1 and 25 and that represented by the $\omega_2$-spinal column IC$_{50}$/ω-hippocampus IC$_{50}$ ratio is also between 1 and 25.

The compounds of the invention may be used in the treatment of complaints associated with disorders of the GABAergic transmission of the GABA$_A$ receptors associated with the $\alpha_5$ sub-unit. The preferred distribution of the ω receptors, associated with the $\alpha_5$ sub-unit of the GABA$_A$ receptor complex, in the olfactory bulb, in limbic structures such as the hippocampus and the hypothalamus, and in the spinal column, suggests that the compounds of the invention may be used in the treatment of olfactory disorders, cognitive disorders, hormonal disorders associated with dysfunction of the hypothalamus, certain emotional disorders and disorders in the perception of pain. They may also be used in the treatment of spasmodism and muscular contractures.

The compounds of the invention may also be used for the treatment of complaints associated with disorders of the GABAergic transmission of the GABA$_A$ receptors associated with the $\alpha_1$, $\alpha_2$ and $\alpha_3$ sub-units, that is to say for the treatment of anxiety, sleeping disorders, epilepsy and disorders of abstinence with respect to alcoholism. Finally, they may be used as anaesthetics, as muscle relaxants or as analgesics.

The present invention also provides a pharmaceutical composition comprising a compound of formula (I) and an excipient, for enteral or parenteral administration, for example in the form of a tablet, coated tablet, gelatin capsule, wafer capsule, drinkable or injectable solution or suspension or suppository, which are dosed to allow a daily administration of 1 to 1000 mg of active substance.

The present invention provides a compound of formula (I) for use in a method of treatment of the human or animal body.

The present invention also provides the use of a compound of formula (I) in the manufacture of a medicament for use in the treatment of a complaint associated with a disorder of the GABAergic transmission of the GABA$_A$ receptors associated with the $\alpha_1$, $\alpha_2$ and $\alpha_3$ sub-units or $\alpha_5$ sub-unit.

The present invention also provides a composition for the treatment of a complaint associated with a disorder of the GABAergic transmission of the GABA$_A$ receptors associated with the $\alpha_1$, $\alpha_2$ and $\alpha_3$ sub-units or with the $\alpha_5$ sub-unit which comprises a compound of formula (I) and a pharmaceutically acceptable excipient.

There is also disclosed a method of treatment of a subject suffering from a complaint associated with a disorder of the GABAergic transmission of the GABA$_A$ receptors associated with the $\alpha_1$, $\alpha_2$, and $\alpha_3$ sub-units or with the $\alpha_5$ sub-unit which comprises administering to that subject an effective amount of a compound of formula (I).

We claim:

1. A compound of formula (I)

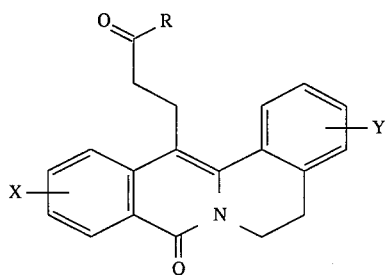

in which

X represents a hydrogen or halogen atom, a $C_1$–$C_3$ alkyl group, a trifluoromethyl group, or a $C_1$–$C_3$ alkoxy group in which case two such alkoxy groups X can be present, Y represents a hydrogen or halogen atom, a $C_1$–$C_3$ alkyl group or a $C_1$–$C_3$ alkoxy group, R represents: a hydroxyl group; a methoxy group; or a group of formula $NR_2R_3$ in which $R_2$ and $R_3$ each independently represents a hydrogen atom, a $C_1$–$C_4$ alkyl group, a 2-methoxyethyl group, a 2-aminoethyl group, a 3-aminopropyl group, a 2-(dimethylamino)ethyl group, a 3-(dimethylamino)propyl group or a 2-piperid-1-ylethyl group, or alternatively $R_2$ and $R_3$ form, together with the nitrogen atom which they are attached, a morpholinyl or pyrrolidinyl ring or a piperazinyl ring optionally substituted in the 4-position with a methyl or (1,1-dimethyl-ethoxy)carbonyl group, in the form of the free base or of a pharmaceutically acceptable acid addition salt thereof.

2. A compound according to claim 1 in which X represents a hydrogen or chlorine atom, a methyl group, a trifluoromethyl group, or a $C_1$–$C_3$ alkoxy group in which case two such alkoxy groups X can be present, and Y represents a hydrogen or chlorine atom, a methyl group or a methoxy group.

3. A compound according to claim 1 in the form of the hydrochloride salt.

4. Process for the preparation of a compound according to claim 1, in which either (i) an anhydride of formula (II)

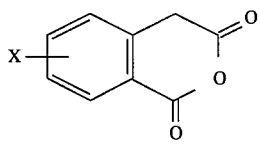

in which X is as defined in claim 1, is reacted with an imine of formula (III)

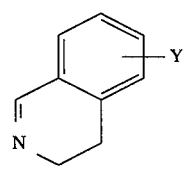

in which Y is as defined in claim 1, to obtain an acid of formula (IV)

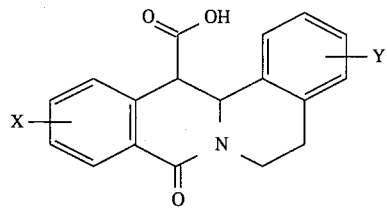

in which X and Y are as defined above, which is esterified with thionyl chloride in methanol, followed by conversion of the ester thus obtained, of formula (V)

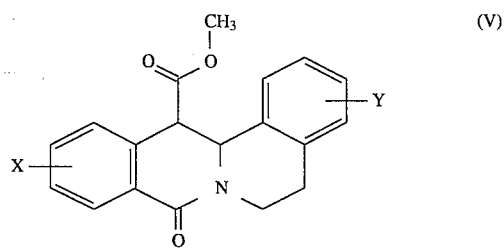

in which X and Y are as defined above, into an alcohol of formula (VI)

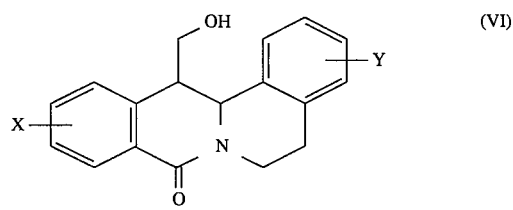

in which X and Y are as defined above, which is then oxidized to an aldehyde of formula (VII)

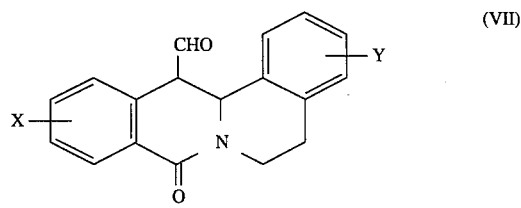

in which X and Y are as defined above, which is treated with methyl (dimethoxyphosphinyl)acetate, and the ester of formula (VIII)

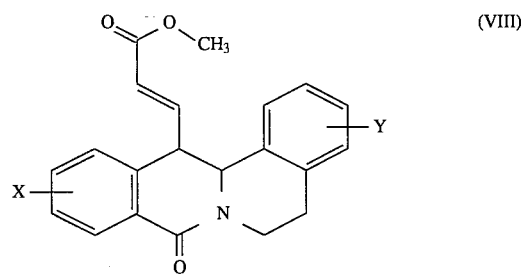

in which X and Y are as defined above, thus obtained is isolated, and then oxidized to an ester of formula (IX)

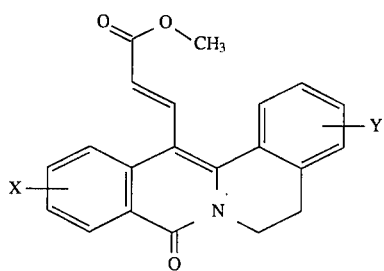 (IX)

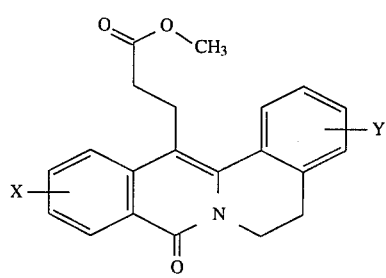 (Ia)

in which X and Y are as defined in claim 1 or (ii) to produce a compound of formula (I) in which X and Y are not methoxy, a dibenzo[a,g]quinolizine of formula (X)

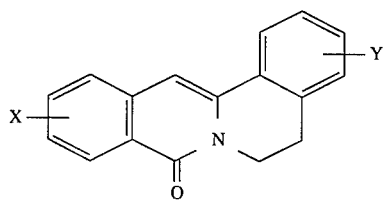 (X)

in which X and Y are as defined above with the exception that they are not methoxy, is treated with phosphorus oxychloride, to obtain an aldehyde of formula (XI)

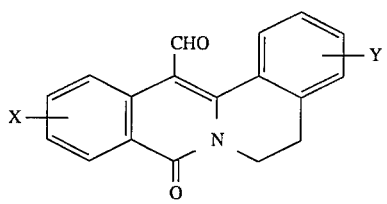 (XI)

in which X and Y are as defined above with the exception that they are not methoxy, which is treated with methyl (dimethoxyphosphinyl)acetate to obtain an ester of formula (IX) as defined above with the exception that X and Y are not methoxy, and, lastly, the ester of formula (IX) from (i) or (ii) is catalytically hydrogenated to obtain an ester of formula (Ia)

which, if desired, is hydrolysed to obtain an acid of formula (Ib)

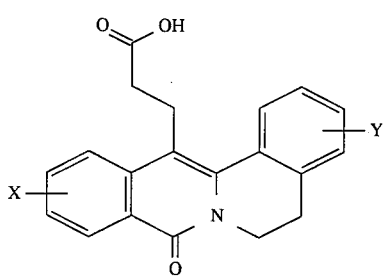 (Ib)

which, if desired, is treated with an amine of formula $HNR_2R_3$ to obtain a compound of formula (I) in which R represents a group of formula $NR_2R_3$ and, if desired, the compound of formula (I) is converted into a pharmaceutically acceptable acid addition salt thereof.

5. A compound of formula (I), prepared by the process according to claim 4.

6. Pharmaceutical composition, which comprises a compound according to claim 1 and an excipient.

7. A method of treatment of a subject suffering from a complaint associated with a disorder of the GABAergic transmission of the $GABA_A$ receptors associated with the $\alpha_1$, $\alpha_2$ and $\alpha_3$ sub-units or with the $\alpha_5$ sub-unit which comprises administering to that subject an effective amount of a compound according to claim 1.

* * * * *